(12) United States Patent
Weissman et al.

(10) Patent No.: US 8,143,051 B2
(45) Date of Patent: Mar. 27, 2012

(54) SYSTEMS AND METHODS FOR MAINTAINING THE DOMINANCE AND INCREASING THE BIOMASS PRODUCTION OF NANNOCHLOROPSIS IN AN ALGAE CULTIVATION SYSTEM

(75) Inventors: Joseph Weissman, Vero Beach, FL (US); Guido Radaelli, Oakland, CA (US); David Rice, Vero Beach, FL (US)

(73) Assignee: Aurora Algae, Inc., Hayward, CA (US)

( * ) Notice: Subject to any disclaimer, the term of this patent is extended or adjusted under 35 U.S.C. 154(b) by 550 days.

(21) Appl. No.: 12/322,668

(22) Filed: Feb. 4, 2009

(65) Prior Publication Data
US 2010/0196995 A1    Aug. 5, 2010

(51) Int. Cl.
*C12N 1/12* (2006.01)
*A01H 13/00* (2006.01)

(52) U.S. Cl. .............. 435/257.1; 435/292.1; 47/1.4; 261/27; 261/30; 261/DIG. 42

(58) Field of Classification Search .................. None
See application file for complete search history.

(56) References Cited

U.S. PATENT DOCUMENTS

| | | | |
|---|---|---|---|
| 1,926,780 A | 9/1933 | Lippincott | |
| 3,468,057 A | 9/1969 | Buisson | |
| 3,897,000 A | 7/1975 | Mandt | |
| 4,003,337 A | 1/1977 | Moore | |
| 4,267,038 A | 5/1981 | Thompson | |
| 4,365,938 A | 12/1982 | Warinner | |
| 4,535,060 A | 8/1985 | Comai | |
| 4,658,757 A | 4/1987 | Cook | |
| 5,105,085 A | 4/1992 | McGuire et al. | |
| 5,130,242 A | 7/1992 | Barclay | |
| 5,338,673 A | 8/1994 | Thepenier et al. | |
| 5,478,208 A | 12/1995 | Kasai | |
| 5,527,456 A | 6/1996 | Jensen | |
| 5,539,133 A | 7/1996 | Kohn et al. | |
| 5,658,767 A | 8/1997 | Kyle | |
| 6,117,313 A | 9/2000 | Goldman | |
| 6,166,231 A | 12/2000 | Hoeksema | |
| 6,372,460 B1 | 4/2002 | Gladue et al. | |
| 6,524,486 B2 | 2/2003 | Borodyanski | |
| 6,579,714 B1 | 6/2003 | Hirabayashi et al. | |
| 6,736,572 B2 | 5/2004 | Geraghty | |
| 6,750,048 B2 | 6/2004 | Ruecker et al. | |
| 6,831,040 B1 | 12/2004 | Unkefer et al. | |
| 7,381,326 B2 | 6/2008 | Haddas | |
| 7,770,322 B2* | 8/2010 | Huntley et al. ............ 47/1.4 |
| 2004/0121447 A1 | 6/2004 | Fournier | |
| 2004/0262219 A1 | 12/2004 | Jensen | |
| 2005/0064577 A1 | 3/2005 | Berzin | |
| 2005/0164192 A1 | 7/2005 | Graham et al. | |
| 2005/0170479 A1 | 8/2005 | Weaver et al. | |
| 2005/0260553 A1 | 11/2005 | Berzin | |
| 2005/0273885 A1 | 12/2005 | Singh et al. | |
| 2006/0045750 A1 | 3/2006 | Stiles | |
| 2006/0122410 A1 | 6/2006 | Fichtali et al. | |
| 2006/0166243 A1 | 7/2006 | Hankamer et al. | |
| 2008/0118964 A1 | 5/2008 | Huntley et al. | |
| 2008/0120749 A1 | 5/2008 | Melis et al. | |
| 2008/0155888 A1 | 7/2008 | Vick et al. | |
| 2008/0160593 A1 | 7/2008 | Oyler | |
| 2008/0293132 A1 | 11/2008 | Goldman et al. | |
| 2009/0011492 A1 | 1/2009 | Berzin | |
| 2009/0029445 A1 | 1/2009 | Eckelberry et al. | |
| 2009/0148931 A1 | 6/2009 | Wilkerson et al. | |
| 2009/0162919 A1 | 6/2009 | Radaelli et al. | |
| 2009/0234146 A1 | 9/2009 | Cooney et al. | |
| 2009/0325270 A1 | 12/2009 | Vick et al. | |
| 2010/0068772 A1 | 3/2010 | Downey | |
| 2010/0183744 A1 | 7/2010 | Weissman et al. | |
| 2010/0196995 A1 | 8/2010 | Weissman et al. | |
| 2010/0210003 A1 | 8/2010 | King | |
| 2010/0260618 A1 | 10/2010 | Parsheh et al. | |
| 2010/0261922 A1 | 10/2010 | Fleischer et al. | |
| 2010/0325948 A1 | 12/2010 | Parsheh et al. | |
| 2010/0327077 A1 | 12/2010 | Parsheh et al. | |
| 2011/0197306 A1 | 8/2011 | Bailey et al. | |

FOREIGN PATENT DOCUMENTS

WO    WO 2009/037683 A1    3/2009

OTHER PUBLICATIONS

Janssen et al., "Enclosed outdoor photobioreactors: light regime, photosynthetic efficiency, scale-up, and future prospects," Biotechnology and Bioengineering, vol. 81, No. 2, p. 193-210, Jan. 20, 2003, Entire document, especially: Fig 4, p. 198 [online]. Retrieved from the Internet on [Oct. 5, 2010]. Retrieved from: <URL: http://onlinelibrary.wiley.com/doi/10.1002/bit.10468/pdf.

(Continued)

*Primary Examiner* — David T Fox
(74) *Attorney, Agent, or Firm* — Carr & Ferrell LLP

(57) ABSTRACT

Systems and methods for maintaining the dominance and increasing the biomass production of *Nannochloropsis* in an algae cultivation system are provided. Exemplary methods include applying an effective amount of ozone to *Nannochloropsis* growing in an algae cultivation system. A further method may include applying a shock amount of ozone above 10 milligrams/liter or higher in the inlet stream flowing into the algae cultivation system. Various exemplary embodiments may include a system for maintaining dominance and increasing the biomass production of *Nannochloropsis* in an algae cultivation system. The system may comprise a processor, and a computer readable storage medium having instructions for execution by the processor. The instructions for execution by the processor cause the processor to maintain dominance and increase biomass production of the *Nannochloropsis* in the algae cultivation system.

12 Claims, 1 Drawing Sheet

OTHER PUBLICATIONS

Strzepek et al., "Photosynthetic architecture differs in coastal and oceanic diatoms," Nature vol. 431, p. 689-692, Oct. 7, 2004. Entire document, especially: abstract, p. 689, col. 2; p. 691, Table 1 [online] Retrieved from the Internet on [Oct. 5, 2010]. Retrieved from: <URL: http://www.nature.com/nature/journal/v431/n7009/pdf/nature02954.pdf.

Zitelli et al., "Mass cultivation of Nannochloropsis sp. in annular reactors," Journal of Applied Phycology vol. 15, p. 107-113, Mar. 2003, Entire document, especially: abstract; p. 110, col. 1-2 [online]. Retrieved from the Internet on [Oct. 5, 2010]. Retrieved from: <URL: http://www.springerlink.com/content/v77772k1mp081775/fulltext.pdf.

Csogor et al., "Light distribution in a novel photobioreactor—modeling for optimization," Journal of Applied Phycology, vol. 13, p. 325-333, May 2001, Entire document, especially: Fig 2, p. 327; Table 1, p. 327; Fig 7, p. 330 [online]. Retrieved from the Internet on [Oct. 5, 2010]. Retrived from: <URL: http://www.springerlink.com/content/p77j66g3j2133522/fulltext.pdf .

Kureshy, et al. "Effect of Ozone Treatment on Cultures of Nannochloropsis oculata, Isochrysis galbana, and Chaetoceros gracilis." Journal of the World Aquaculture Society, Dec. 1999, vol. 30, No. 4, pp. 473-480; p. 473, Abstract; p. 475, "Nannochloropsis oculata" Section; p. 476, Table 1; p. 476, Table 2; p. 479, left column, para 2.

NCBI entry EE109892 (Jul. 27, 2006) [Retrieved from the Interenet on Oct. 19, 2009; <http://www.ncbi.nlm.nih.gov/nucest/EE109892?ordinalpos=1&itoo1=EntrezSystem2.PEntrez.Sequence.Sequence_ResultsPanel.Sequence_RVDocSum>].

Knuckey et al., "Production of Microalgal Concentrates by Flocculation and Their Assessment as Aquaculture Feeds," Aquacultural Engineering 35 (2006) 300-313.

Grima et al., "Recovery of Microalgal Biomass in Metabolites: Process Options and Economics," Biotechnology Advances 20 (2003) 491-515.

Lee et al. Isolation and Characterization of a Xanthophyll Aberrant Mutant of the Green Alga Nannochloropsis oculata Marine Biotechnology vol. 8, 238-245 (2006) (p. 239 col. 1 para 1; p. 239 col. 2 para 4; p. 240 col. 1 para 2; p. 242 col. 2 para 2; p. 241 Table 1, Fig 2; p. 242 Table 2).

Berberoglu et al. Radiation characteristics of Chlamydomonas reinhardtii CC125 and itstruncated chlorophyll antenna transformants tla1, tlaX and tla1-Cw+. International Journal of Hydrogen Energy.2008 vol. 33 pp. 6467-6483, especially the abstract.

Ghirardi et al. Photochemical apparatus organization in the thylakoid membrane of Hordeum vulgare wild type and chlorophyll b-less chlorine f2 mutant. Biochimica et Biophysica Acta (BBA)—Bioenergetics. vol. 851, Issue 3, Oct. 8, 1986, pp. 331-339 (abstract only).

Steinitz et al. A mutant of the cyanobacterium Plectonema boryanum resistant to photoxidation. Plant Science Letters. vol. 16, Issues 2-3, Oct. 1979, pp. 327-335 (abstract only).

Koller et al. Light Intensity During Leaf Growth Affects Chlorophyll Concentration and CO2 Assimilation of a Soybean Chlorophyll Mutant. Crop Sci. 1974. vol. 14 pp. 779-782 (abstract only).

Shikanai et al. Identification and Characterization of Arabidopsis Mutants with Reduced Quenching of Chlorophyll Fluorescence. Plant and Cell Physiology, 1999, vol. 40, No. 11. pp. 1134-1142 (abstract only) .

Santin-Montanaya, I. Optimal growth of Dunaliella primolecta in axenic conditions to assay herbicides, Chemosphere, 66, 2006, pp. 1315-1322.

Felix, R. Use of the cell wall-less alga Dunaliella bioculata in herbicide screening tests, Annals of Applied Biology, 113, 1988, pp. 55-60.

Janssen, M. Photosynthetic efficiency of Dunaliella tertiolecta under short light/dark cycles, Enzyme and Microbial Technology, 29, 2001, pp. 298-305.

Saenz, M.E. Effects of Technical Grade and a Commercial Formulation of Glyphosate on Algal Population Growth, Bulletin of Environmental Contamination Toxicology, 1997, pp. 638-644, vol. 59.

Anderson, Robert A., Algal Culturing Techniques, 2005. p. 208.

Applying [online] retrieved from: http://www.merriam-webster.com/dictionary/applying, on May 21, 2011; 3 pages.

Ben-Amotz, Ami. "Large-Scale Open Ponds" presented at the NREL-AFOSR Joint Workshop on Algal Oil for Jet Fuel Production in Feb. 2008.

Cohen (Chemicals from microalgae 1999, CRC Press, pp. 49 and 51 in part).

Ebeling et al. "Design and Operation of a Zero-Exchange Mixed-Cell Raceway Production System" 2nd International Sustainable Marine Fish Culture Conference and Workshop, Oct. 19-21, 2005. Entire Document.

Ebeling et al. "Mixed-Cell Raceway: Engineering Design Criteria, Construction, and Hydraulic Characterication" North American Journal of Aquaculture 2005; 67: 193-201. Abstract only Labatut et al. "Hydroynmaics of a Large-Scale Mixed-Cell Raceway (MCR): Exoerimental Studies" Aquacultural Engineering vol. 37, Issue 2, Sep. 2007, pp. 132-143, esp: abstract, p. 134, p. 135, p. 136, p. 137, p. 138, p. 142, Figs. 2,4,5 Table 2.

\* cited by examiner

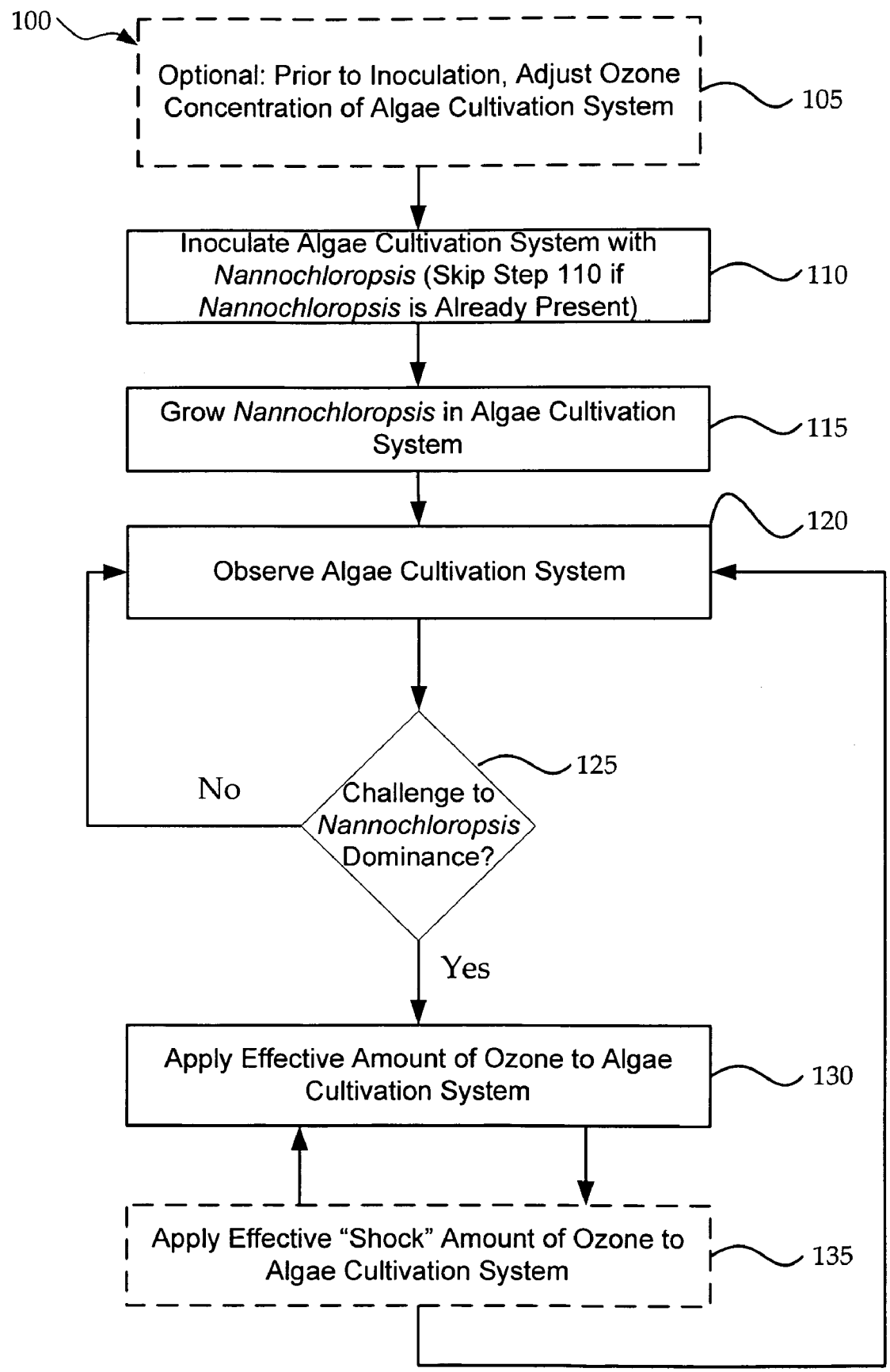

SYSTEMS AND METHODS FOR MAINTAINING THE DOMINANCE AND INCREASING THE BIOMASS PRODUCTION OF NANNOCHLOROPSIS IN AN ALGAE CULTIVATION SYSTEM

BACKGROUND OF THE INVENTION

1. Field of the Invention

This invention relates to algae cultivation systems, and more specifically to systems and methods for maintaining the dominance and increasing the biomass production of *Nannochloropsis* in an algae cultivation system.

2. Description of Related Art

*Nannochloropsis* cultures are subject to contamination by competing species and predators. Optimizing an algae cultivation system for the growth of *Nannochloropsis* to increase its resistance to competing species and predators results in fewer collapses, or crashes, of the *Nannochloropsis* culture. The maintenance of a stable mass culture of *Nannochloropsis* maximizes the accumulation of biomass. This accumulation of biomass is highly desirable for the production of biofuels and higher value products, such as, but not limited to, animal feed, fish meal formulations, carotenoids, polyunsaturated fatty acids ("PUFAs"), and products for the cosmetic and pharmaceutical industries. The exemplary embodiments described herein accomplish these objectives.

SUMMARY OF THE INVENTION

Systems and methods for maintaining the dominance and increasing the biomass production of *Nannochloropsis* in an algae cultivation system are provided. Exemplary methods include applying an effective amount of ozone to *Nannochloropsis* growing in an algae cultivation system. The effective amount of ozone results in an approximate initial concentration of between 0.1 milligrams/liter and 10 milligrams/liter of ozone in an inlet stream flowing into the algae cultivation system. The inlet stream may include an existing algae culture comprising *Nannochloropsis*, predators and/or invaders. A further method may include applying a shock amount of ozone above 10 milligrams/liter or higher in the inlet stream flowing into the algae cultivation system.

Various exemplary embodiments may include a system for maintaining dominance and increasing the biomass production of *Nannochloropsis* in an algae cultivation system. The system may comprise a processor, and a computer readable storage medium having instructions for execution by the processor. The instructions for execution by the processor cause the processor to maintain dominance and increase biomass production of the *Nannochloropsis* in the algae cultivation system. The processor is connected to the computer readable storage medium. The processor executes the instructions on the computer readable storage medium to apply an effective amount of ozone to the inlet stream flowing into the algae cultivation system (can be measured through the use of an ORP meter). The processor may execute other instructions described herein and remain within the scope of contemplated embodiments.

BRIEF DESCRIPTION OF THE DRAWINGS

FIG. 1 shows a flow chart for an exemplary method of using ozone to maintain the dominance and increase the biomass production of *Nannochloropsis* in an algae cultivation system.

DETAILED DESCRIPTION OF THE INVENTION

By utilizing the unexpected discoveries that *Nannochloropsis* tolerates a relatively high exposure to ozone in comparison to its competing species (or invaders) and predators, the exemplary systems and methods described herein optimize an algae cultivation system for the dominance of *Nannochloropsis*. Further, the various systems and methods described herein maximize the production of biomass by *Nannochloropsis*, which is highly desirable for large volume applications, such as for the production of biofuels.

FIG. 1 shows a flow chart for an exemplary method 100 of using ozone to maintain the dominance and increase the biomass production of *Nannochloropsis* in an algae cultivation system.

At optional step 105, before the algae cultivation system is inoculated with *Nannochloropsis*, the ozone concentration of the algae cultivation system may be adjusted. Such a step may be viewed as a prophylactic measure. The ozone concentration of the algae cultivation system may be adjusted via the inlet stream that feeds into the algae cultivation system. For example, ozone may be added to the inlet stream by using a commercial ozone generator with an accompanying liquid pump, venturi and air dryer. The inlet stream may comprise fresh water, salt water, or a mixture thereof. The inlet stream may also comprise *Nannochloropsis*, predators and/or invaders. Applying an effective amount of ozone to the inlet stream may result in an initial ozone concentration of the inlet stream of between approximately 0.1 milligrams/liter to 10 milligrams/liter, which feeds into the algae cultivation system.

At step 110, the algae cultivation system is inoculated with *Nannochloropsis* (note: step 110 may be skipped if *Nannochloropsis* is already present, e.g., an existing pond, vessel, photobioreactor, etc. with *Nannochloropsis*). According to various exemplary embodiments, the algae cultivation system may be an open pond, a closed pond and/or a photobioreactor. Further, the *Nannochloropsis* culture may comprise one or more strains of the genus *Nannochloropsis*. Outdoor *Nannochloropsis* cultures may be started with the addition of an initial, small amount of pure unialgal (virtually free from unwanted contaminant organisms) *Nannochloropsis*. Such an inoculum may be generated in a controlled environment, such as in a laboratory or in a closed system. The inoculum may be introduced into a larger volume of water that may have a predetermined ozone concentration (e.g., using step 105 as described herein) chosen to be optimal for the *Nannochloropsis* growth and/or chosen to be suboptimal for competing strains.

At step 115, the *Nannochloropsis* is grown in the algae cultivation system. According to various embodiments, the *Nannochloropsis* culture may require light (natural or artificially supplied) for growth, as well as nutrients. Other parameters such as pH should be within acceptable ranges. The basic elements typically required for *Nannochloropsis* growth may include carbon, oxygen, hydrogen, nitrogen, sulfur, phosphorous, potassium, magnesium, iron and traces of several other elements.

The required nutrients for *Nannochloropsis* growth may be contained in the water, supplied subsequently in dilution waters, or supplied independently of the dilution waters, in a concentration sufficient to allow *Nannochloropsis* to grow and reach a desired final density. The amount of nutrients needed to yield a prescribed *Nannochloropsis* density may be determined by the cell quota for that nutrient. That is, by the per cent of the algal dry mass that is comprised of the element contained in the nutrient. The inverse of the cell quota is called the algae growth potential for that nutrient or element.

For instance, if the desired final density is 1 gram/liter and the *Nannochloropsis* strain under consideration contains ten percent (10%) nitrogen in its biomass (i.e., a cell quota of 0.1), then the initial concentration of the atomic nitrogen in the culture should be at least 0.1 gram/liter. The same calculation may be performed for all nutrients to establish their initial concentration in the culture.

In various embodiments, a wide variety of systems utilized for the mass culturing of algae may be optimized for *Nannochloropsis* growth. The time-averaged light intensity to which *Nannochloropsis* may be exposed may be adjusted by changes in the mixing intensity and in the optical depth of the apparatus. In panel-shaped modular photobioreactors, the latter may be performed by controlling the distance between two consecutive panels. On the other hand, the optical depth in open ponds may be the depth of the pond. Similarly, the temperature in closed photobioreactors may be precisely controlled by means of indirect heat exchange. In open ponds, the temperature may be controlled by adjusting culture depth. After two to ten days, *Nannochloropsis* may reach a productive operating density depending on light intensity, temperature, and the starting inoculum size.

Once the *Nannochloropsis* is grown to a desired density, according to some embodiments, it may either be removed (and a new culture may be started with a new inoculum), or it may be diluted according to a prescribed schedule or rate. In the first case, culturing may be performed in a batch mode and may require frequent re-inoculation. In the latter case, culturing may be performed in a continuous or a semi-continuous fashion, depending on the way the dilution is performed. For example, assuming that the desired dilution rate is fifty percent (50%) per day of the culture volume, culture dilution may take place in one or more of several techniques. Culture dilution may take place continuously over the day (or over part of the day) at a constant or at a variable rate. Culture dilution may alternatively take place semi-continuously once a day (i.e., fifty percent (50%) of the culture is removed and replaced with a new growth medium in a short period of time every day); semi-continuously twice a day (i.e., twenty-five percent (25%) of the culture is removed each time at two different times every day); or semi-continuously at any other desired frequency over the day. In some embodiments, culture dilution may comprise removing the *Nannochloropsis* culture medium from the growth system—whether this is in an open pond or in a closed photobioreactor—and replacing this portion with fresh medium, which may contain all of the nutrients in the quantity sufficient for the growth of the *Nannochloropsis* between two consecutive dilutions.

At step 120, after the algae cultivation system is inoculated with *Nannochloropsis* and the *Nannochloropsis* is grown to a desired density (e.g., as described in connection with step 110 and step 115), the algae cultivation system may be observed (e.g., visually with a naked eye, microscopically, and/or analytically, including the taking and analysis of samples). Such observations or sampling may take place every minute, hourly, daily, every other day, three times a week, weekly, and/or on any other suitable basis. In connection with this process, one or more determinations may be made as to a relative level or amount of predators and/or invaders in comparison to an actual and/or desired density or dominance of *Nannochloropsis*.

At step 125, a determination is made whether *Nannochloropsis* dominance in the algae cultivation system is being challenged by predators and/or invaders. Based upon this determination, a decision may be made whether to adjust the ozone concentration of the algae cultivation system. If the level or amount of predators and/or invaders is less than a prescribed level, the ozone concentration of the algae cultivation system may not require the adjustment described in connection with step 130 and/or step 135 and the algae cultivation system may continue to be observed as described in connection with step 120.

At step 130, if the level or amount of predators and/or invaders exceeds an actual or desired level, the ozone concentration of the algae cultivation system may be adjusted. The ozone concentration of the algae cultivation system may be adjusted via the inlet stream that feeds into the algae cultivation system. For example, ozone may be added to the inlet stream by using a commercial ozone generator with an accompanying liquid pump, venturi and air dryer. The inlet stream may comprise fresh water, salt water, or a mixture thereof. The inlet stream may also comprise *Nannochloropsis*, predators and/or invaders. Applying an effective amount of ozone to the inlet stream may result in an initial ozone concentration of the inlet stream of between approximately 0.1 milligrams/liter to 10 milligrams/liter, which feeds into the algae cultivation system.

At alternative step 135, if the level or amount of predators and/or invaders exceeds an actual or desired level, the ozone concentration of the algae cultivation system may be adjusted by applying an effective "shock" amount of ozone. The ozone concentration of the algae cultivation system may be adjusted via the inlet stream that feeds into the algae cultivation system. Applying an effective shock amount of ozone to the inlet stream may result in an initial ozone concentration of the inlet stream above 10 milligrams/liter, which feeds into the algae cultivation system. An unexpected result observed via the experiments described herein is that *Nannochloropsis* cultures exposed to extremely high levels of ozone (above 30 milligrams/liter) recover (i.e., the *Nannochloropsis* cultures were not killed), provided the exposure to the ozone is not prolonged. In particular, when a high concentration of ozone (e.g., above 10 milligrams/liter) is applied to the algae cultivation system, the *Nannochloropsis* may display zero productivity in the first two days following the administration of the ozone before it exhibits productivity in the following days until normal productivity is restored. Note: steps 130 and 135 may be performed in alternating or rotating fashion, provided the ozone concentration is properly observed.

If an effective amount or an effective shock amount of ozone is applied to the algae cultivation system, post-treatment observations may be made. Generally, if the density or dominance of *Nannochloropsis* increases, one may assume the application of ozone was effective (i.e. an effective protocol). If the density or dominance of *Nannochloropsis* decreases, one may assume the application of an effective amount of ozone was ineffective (i.e. an ineffective protocol), and consider the application of a second effective amount of ozone.

Various embodiments may include a system for maintaining dominance and increasing biomass production of *Nannochloropsis* in an algae cultivation system. The system may include a communications interface, a computer readable storage medium, a processor, and an ozone application means, such as an ozone generator and associated equipment. The computer readable storage medium may further comprise instructions for execution by the processor. The instructions for execution by the processor cause the processor to maintain dominance and increase biomass production of the *Nannochloropsis* in the algae cultivation system. For example, the processor may execute the instructions on the computer readable medium to apply an effective amount or an effective shock amount of ozone to an inlet stream flowing into the algae cultivation system. The processor may execute other instructions described herein and remain within the scope of contemplated embodiments.

Another embodiment may include a computer readable storage medium having a computer readable code for operating a computer to perform a method of maintaining dominance and increasing biomass production of *Nannochloropsis* in an algae cultivation system. For example, the method may comprise the step of applying an effective amount or an effective shock amount of ozone to an inlet stream flowing into the algae cultivation system.

Examples of computer readable storage medium may include discs, memory cards, servers and/or computer discs. Instructions may be retrieved and executed by a processor. Some examples of instructions include software, program code, and firmware. Instructions are generally operational when executed by the processor to direct the processor to operate in accord with embodiments of the invention. Although various modules may be configured to perform some or all of the various steps described herein, fewer or more modules may be provided and still fall within the scope of various embodiments.

EXAMPLES

In the following examples, *Nannochloropsis* was grown in outdoor, open, three-square meter ponds in Vero Beach, Fla. The climate in Vero Beach is semitropical, with mild, cool winters and hot, humid summers. It is a challenging climate for keeping outdoor algal cultures stable and productive. The overnight warmth encourages predation by protozoa, rotifers, and crustaceans. The humidity allows the airborne transport of competing algae, and thus increases the rate of invasion.

Example One

Ozone was added to an algal cultivation system using a commercial ozone generator with accompanying liquid pump, venturi, and air dryer. The machine used was a small model capable of generating 10 grams of ozone per hour. The flow rate of liquid through the generator was about 16 liters per minute. At fifty percent (50%) of maximal ozone generation, the concentration of ozone in the liquid after one pass through the ozone generator was 4.6 mg/L, and at 100% was 9.6 mg/L.

Two three-square meter ponds were started by taking 500 L of culture from a larger pond and passing it through the ozone generator once. One pond was started with the ozonator setting at 50%, the other pond was started with the ozonator setting at 100%. The original algal culture had numerous clumps of *Nannochloropsis*, cell debris, various diatoms, and some ciliated protozoa grazers. After the one pass-through the ozone generator, only single cells of *Nannochloropsis* survived. The clumps were completely broken up, the diatoms and grazers were killed, and the cell debris was oxidized.

The two algal cultures were allowed to grow for two days without dilution, but with nutrient addition to see whether the ozone treatment changed the production of biomass and the subsequent stability of the cultures. After two days of batch growth, each pond was diluted one third per day and recirculated each day through the ozone generator for 30 minutes. During this time period about 500 L, or one volume equivalent was treated. As before, one pond was passed through the machine at 50% setting and one at 100% setting. This treatment continued for three days, during which time both ponds were about equal in production of biomass, at a level 20% above that of a control pond, and showed no ill effects from the ozone.

Example Two

An ozone skid was assembled on-site utilizing a dry air feed ozone generator capable of producing 10 g/h of ozone. The intention of the tests was to demonstrate the effectiveness of ozone disinfection and *Nannochloropsis* resistance to concentrations of ozone.

A small pump was connected to the system with the ozone added to the liquid recycle line via a Mazzei gas to liquid injector capable of flow rates between 13.2-28.35 lpm@pressures ranging from 15-25 psi. Tests were run on ponds D4 (3 m$^2$ surface area), MP1 (3 m$^2$ surface area), and 25A (25 m$^2$ surface area) with salinities ranging from 20-24 ppt using flow rates of 13.2 and 15.6 lpm@20 psi. The ozonator is equipped with a variable transformer that offers the ability to vary ozone dosage between 0-100%. Tests were run at ozone concentrations of 25%, 50%, 75%, and 100% at flow rates of 13.2 and 15.6 lpm. Respective ozone dosages at these flow rates are listed in the tables below.

| Ozone dosages @ 13.2 lpm | |
|---|---|
| Ozone Concentration (%) | Ozone Concentration (milligrams per liter) |
| 25% | 0.32 mg/l |
| 50% | 0.63 mg/l |
| 75% | 0.94 mg/l |
| 100% | 1.26 mg/l |

| Ozone dosages @ 15.6 lpm | |
|---|---|
| Ozone Concentration (%) | Ozone Concentration (milligrams per liter) |
| 25% | 0.27 mg/l |
| 50% | 0.53 mg/l |
| 75% | 0.80 mg/l |
| 100% | 1.06 mg/l |

Productivity results of the three pond systems run at the high concentrations are listed below:

| Pond D4 Ozone Test Results | | | |
|---|---|---|---|
| Date | Total Concentration O$_3$ (mg O$_3$) | Volume Recycled (liters) | Productivity (g/m$^2$/day) |
| Jul. 09, 2008 | 500 | 470 | 15.4 |
| Jul. 10, 2008 | 500 | 470 | 16.1 |
| Jul. 11, 2008 | 500 | 470 | 16.0 |
| Jul. 12, 2008 | 500 | 470 | 8.4 |
| Jul. 13, 2008 | 500 | 470 | 12.2 |
| Jul. 14, 2008 | 500 | 470 | 14.9 |

| Pond MP1 Ozone Test Results | | | |
|---|---|---|---|
| Date | Total Concentration O$_3$ (mg O$_3$) | Volume Recycled (liters) | Productivity (g/m$^2$/day) |
| Jul. 09, 2008 | 500 | 470 | 13.3 |
| Jul. 10, 2008 | 500 | 470 | 17.2 |

-continued

Pond MP1 Ozone Test Results

| Date | Total Concentration $O_3$ (mg $O_3$) | Volume Recycled (liters) | Productivity (g/m²/day) |
|---|---|---|---|
| Jul. 11, 2008 | 500 | 470 | 16.9 |
| Jul. 12, 2008 | 500 | 470 | 9.0 |
| Jul. 13, 2008 | 500 | 470 | 16.0 |
| Jul. 14, 2008 | 500 | 470 | 13.4 |

Pond 25A Ozone Test Results

| Date | Total Concentration $O_3$ (mg $O_3$) | Volume Recycled (liters) | Productivity (g/m²/day) |
|---|---|---|---|
| Jul. 09, 2008 | 5950 | 5615 | 16.1 |
| Jul. 10, 2008 | 5950 | 5615 | 4.6 |
| Jul. 11, 2008 | 5950 | 5615 | −8.3* |
| Jul. 12, 2008 | 5950 | 5615 | 12.2 |
| Jul. 13, 2008 | 5950 | 5615 | 10.7 |
| Jul. 14, 2008 | 5950 | 5615 | 8.0 |

(*pond temperature reached 39° C.)

Observational Data.

During testing of the smaller 3 m² ponds, D4 and MP1, it was witnessed that at the concentrations of ozone tested, most if not all of the diatoms and grazers present were adversely affected after exposure to ozone resulting in their elimination. *Nannochloropsis* was unaffected by ozone at these dosages. After the daily repeated exposure to ozone in these small ponds, clumps did form in large numbers until the pond was dominated by large clumps.

In the larger 25 m² pond, 25A, grazers and diatoms were similarly affected, but clumping did not become as dramatic of a problem. The entire volume of the pond did not receive exposure as did the volumes of the smaller ponds, since only a side stream was taken out and treated.

Using the skid mounted system as an in-situ transfer treatment to inoculate new ponds was also tested with very favorable results. Both D4 (3 m²) and MP1 (3 m²) were filled with ozone treated inoculums from one of the larger ponds that had large amounts of clumps and decreasing productivity. The effect of this was that most of the clumps (>80%) were broken up and the grazers present inside of the clumps were destroyed as well as free grazers and diatoms in the solution with no effect on *Nannochloropsis*.

Exemplary Laboratory Protocol for *Nannochloropsis* Culture

Algal cultivation: 800 ml cultures are maintained in one inch thick Roux flasks with continuous magnetic stirring. Continuous illumination at 700 MicroEinsteins per meter squared per second is provided by four 54-watt T5 fluorescent bulbs rated with a correlated color temperature of 5000K. 1% $CO_2$ is bubbled through scintered glass spargers at a rate sufficient to maintain a pH between 7.0 and 8.5. Photoautotrophic growth is maintained on UFM media formulated with artificial seawater (35 g/L Instant Ocean) containing 720 mg/L urea, 168 mg/L $K_2HPO_4$, 1.5 ml/L of a metals solution and 1 ml/L of a vitamin solution. The metals solution contains 39.7 g/L Fe(III)Cl3(6H2O), 30.0 g/L EDTA, 1.2 g/L MnCl2(4H2O), 0.08 g/L CoCl2(6H2O), 0.16 g/L ZnSO4(7H2O), 0.067 g/L CuSO4(5H2O), 0.023 g/L Na2MoO4(2H2O). The vitamins solution contains 0.001 g/L vitamin B12, 0.001 g/L Biotin, and 0.2 g/L Thiamine. Cultures are diluted by exchanging 400 ml of culture with fresh media every day at the same time. From the 400 ml that are removed, the dry biomass concentration is determined as below.

Determination of culture biomass concentration: A sample of the culture between 0.5 and five milliliters is vacuum filtered through a pre-rinsed and pre-ashed Whatman GF/C glass microfiber filter disc. The cake is rinsed with twenty milliliters of 0.7M ammonium formate and dried for at least 2 hours at 105° C. The dried sample is weighed on an analytical balance and then ashed at 550° C. for at least 4 hours. The post ash weight is subtracted from the pre-ash weight and divided by the volume of the sample to get the ash-free dry biomass density in milligrams per milliliter.

Given the dilution volume and the previous day's dry biomass concentration, the current day's dry biomass concentration can be used to establish the culture's dry biomass productivity in grams per liter per day. This productivity value can then be compared across different experimental conditions.

While various embodiments are described herein, it should be understood that they are presented by way of example only, and not limitation. Thus, the breadth and scope of a preferred embodiment should not be limited by any of the described exemplary embodiments.

What is claimed is:

1. A method for maintaining dominance and increasing biomass production of *Nannochloropsis* in an algae cultivation system, the method comprising:

diverting a volume of culture from the algae cultivation system, the volume including the *Nannochloropsis* and the volume circulating back into the algae cultivation system via an inlet stream; and applying an effective amount of ozone to the inlet stream of the algae cultivation system, the effective amount of the ozone resulting in an approximate initial concentration of between 0.5 milligrams/liter and 10 milligrams/liter of ozone in the inlet stream flowing into the algae cultivation system.

2. The method of claim 1, wherein the inlet stream further comprises an invader.

3. The method of claim 1, wherein the inlet stream further comprises a predator.

4. The method of claim 1, the method further comprising visually observing the algae cultivation system for a presence of predators or invaders.

5. The method of claim 4, the method further comprising applying the effective amount of the ozone if the presence of predators or invaders appears to challenge dominance of the *Nannochloropsis* growing in the algae cultivation system.

6. The method of claim 1, wherein the algae cultivation system includes seawater.

7. The method of claim 1, wherein the algae cultivation system includes fresh water.

8. The method of claim 1, wherein the algae cultivation system includes a mixture of seawater and fresh water.

9. The method of claim 1, wherein the algae cultivation system is in a photobioreactor.

10. The method of claim 1, wherein the algae cultivation system is in an open pond.

11. The method of claim 1, wherein the algae cultivation system is in an open vessel.

12. The method of claim 1, wherein the algae cultivation system is in a closed vessel.

* * * * *